US007732425B2

(12) United States Patent
Matsuo et al.

(10) Patent No.: US 7,732,425 B2
(45) Date of Patent: Jun. 8, 2010

(54) PHARMACEUTICAL COMPOSITION FOR OPHTHALMIC USE

(75) Inventors: Toshihiko Matsuo, Okayama (JP); Masashi Kurimoto, Okayama (JP); Hiroshi Yamauchi, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 10/393,947

(22) Filed: Mar. 24, 2003

(65) Prior Publication Data

US 2003/0186931 A1    Oct. 2, 2003

Related U.S. Application Data

(63) Continuation of application No. 09/941,854, filed on Aug. 30, 2001, now Pat. No. 6,555,526.

(30) Foreign Application Priority Data

Sep. 14, 2000    (JP)    ............................. 2000-280023

(51) Int. Cl.
*A61K 31/715*    (2006.01)
(52) U.S. Cl. ........................................ 514/53; 514/912
(58) Field of Classification Search .................. 514/53, 514/912
See application file for complete search history.

(56) References Cited

U.S. PATENT DOCUMENTS 5,472,863 A    12/1995    Maruta et al.
6,656,920 B2*    12/2003    Fox et al. ...................... 514/53

FOREIGN PATENT DOCUMENTS

| EP | 0 486 315 A2 | 5/1992 |
|----|---|---|
| EP | 0 606 753 A2 | 7/1994 |
| EP | 0 671 470 A2 | 9/1995 |
| EP | 0 674 005 A2 | 9/1995 |
| EP | 0 688 866 A1 | 12/1995 |
| EP | 0 688 867 A2 | 12/1995 |
| EP | 0 697 461 A1 | 2/1996 |
| EP | 0 709 461 A1 | 5/1996 |
| JP | 4 179490 | 6/1992 |
| JP | 7 143876 | 6/1995 |
| JP | 7-213283 | 8/1995 |
| JP | 7-298880 | 11/1995 |
| JP | 7-322883 | 12/1995 |
| JP | 8-66187 | 3/1996 |
| JP | 8-66188 | 3/1996 |
| JP | 8-84586 | 4/1996 |
| JP | 8-336388 | 12/1996 |
| JP | 9-235233 | 9/1997 |
| JP | 10 072376 A | 3/1998 |
| WO | WO 97/24129 A1 | 7/1997 |

OTHER PUBLICATIONS

T. Matsuo, "Trehalose Protects Corneal Epithelial Cells from Death by Drying", *British Journal of Ophthalmology*, 2001, pp. 610-612, vol. 85, No. 5.
Database WPI, Derwent Publications Ltd., Abstract for JP 06 256219, Sep. 13, 1994, applicant Hisamitsu Pharm Co Ltd, title "Medicate Composition Administer . . . ".
Patent Abstracts of Japan, European Patent Office, for JP 10 072376, Mar. 17, 1998, applicant Ofutekusu: KK, title "Eye Drop Aqueous Solution Comprising . . . ".

* cited by examiner

*Primary Examiner*—Zohreh A Fay
(74) *Attorney, Agent, or Firm*—Browdy and Neimark PLLC

(57) ABSTRACT

An ophthalmic pharmaceutical composition comprising trehalose as an effective ingredient and a pharmaceutically-acceptable carrier. The pharmaceutical composition is a safe, long-term continuously-administrable, therapeutic and/or prophylactic agent for the ophthalmologic clinical symptoms and signs in Sjögren syndrome.

3 Claims, No Drawings

PHARMACEUTICAL COMPOSITION FOR OPHTHALMIC USE

RELATED APPLICATIONS

This is a continuation of parent application Ser. No. 09/941,854, filed Aug. 30, 2001 now U.S. Pat. No. 6,555,526.

BACKGROUND OF THE INVENTION

1. Field of the Invention

The present invention relates to the treatment in an ophthalmologic field, more particularly, to ophthalmic pharmaceutical compositions for treating and/or preventing the ophthalmologic clinical symptoms and signs in Sjögren syndrome.

2. Description of the Prior Art

Sjögren syndrome is one of the frequently diagnosed diseases and is often found particularly in older ages. It is estimated that patients with such a syndrome will increase in number more and more as coming into the aging society. As characteristic features, Sjögren syndrome is accompanied by the invasion of lymphocytes into the lacrimal gland and the salivary gland, and the disruption of adenocytes, and is characterized mainly by dry eye and dry mouth. Sjögren syndrome is a cryptogenic disease or the like and is highly speculated as an autoimmune disease, and the criterion has been already established. The ophthalmologic clinical symptoms of Sjögren syndrome are, for example, foreign body sensation, burning, and itching. Treatments for Sjögren syndrome now used predominantly are symptomatic therapies such as the application of artificial tears and the wear of goggles and glasses for preventing dry eye. When the symptoms of patients with these treatments are not improved, they are then treated mainly with other symptomatic therapies such as surgeries and the administration of steroids and immunosuppressants in combination, which may restrict patient's normal social life because these therapies would require hospitalization, doctor's advice, or therapeutic devices. Conventional ophthalmic solutions used generally in the ophthalmologic field are easily portable and readily usable when in use, and therefore ophthalmic solutions, containing sodium hyaluronate for treating the ophthalmologic clinical symptoms and signs in Sjögren syndrome, have been commercialized recently, however, any satisfactory ophthalmic pharmaceutical composition for treating and/or preventing the syndrome has not been provided yet.

SUMMARY OF THE INVENTION

The object of the present invention is to provide an ophthalmic pharmaceutical composition with a satisfactory therapeutic and/or prophylactic effect on the ophthalmologic clinical symptoms and signs in Sjögren syndrome, as well as advantageous usefulness and safety; and more particularly to an ophthalmic solution, ointment, and eyewash.

In view of the foregoing, the present inventors screened substances which have a satisfactory therapeutic and/or prophylactic effect on the ophthalmologic clinical symptoms and signs in Sjögren syndrome and have safety even when used for a relatively-long period of time. As a result, the present inventors unexpectedly found that trehalose, which is widely used in food products and cosmetics, exerts an outstanding therapeutic and/or prophylactic effect on the clinical symptoms and signs in Sjögren syndrome without any side effect even after a relatively-long time administration; the present invention solves the above object by the ophthalmic pharmaceutical composition comprising trehalose as an effective ingredient.

Trehalose, a disaccharide composed of two glucose molecules linked together at their reducing residues, has 3-types of optical isomers of $\alpha,\alpha$-trehalose, $\alpha,\beta$-trehalose, and $\beta,\beta$-trehalose, which are hereinafter called "trehalose", if specified otherwise. In the natural world, trehalose is widely distributed in bacterial, plant, and animal worlds. In the field of food products, trehalose has been being greatly increased in demand because of its remarkable characteristic features such as relatively-low sweetness, prevention of retrogradation of starches, and prevention of denaturation of proteins during freezing/drying. In the field of cosmetics, the use of trehalose has been wide-spreading because of its satisfactory moisture-retaining ability, and the safety of oral administration and dermatological application of trehalose has been already confirmed. However, as for the physiological functions of trehalose, there have only been known the improvement of osteoporosis and the regulation of metabolism of serum fatty acids, while in the field of ophthalmology, only reported is the action of trehalose to protect cells in the corneal endothelium and the corneal epithelium susceptible to damage induced by ophthalmic surgeries as disclosed in Japanese Patent Kokai No. 235,233/97.

As described above, trehalose per se is a well-known compound, however, it was firstly found in the present invention that trehalose exerts a satisfactory therapeutic and/or prophylactic effect on the ophthalmologic clinical symptoms and signs in Sjögren syndrome.

DETAILED DESCRIPTION OF THE INVENTION

The present invention relates to an ophthalmic pharmaceutical composition for treating and/or preventing the ophthalmologic clinical symptoms and signs in Sjögren syndrome, which comprises trehalose as an effective ingredient. As described above, there exist three types of optical isomers of trehalose, i.e., $\alpha,\alpha$-trehalose, $\alpha,\beta$-trehalose, and $\beta,\beta$-trehalose, which all exert an effective therapeutic and/or prophylactic effect on the ophthalmologic clinical symptoms and signs in Sjögren syndrome, and therefore one or more of these optical isomers can be arbitrarily used in combination in the present invention. In the ophthalmic pharmaceutical compositions of the present invention, each of the optical isomers of trehalose can be used alone or two or more of them can be used in combination independently of their combination use and preparation methods, as long as they contain an effective amount of trehalose.

Any trehalose can be used in the present invention independently of its preparation methods and origin, as long as it does not spoil the present object. Examples of the methods for producing $\alpha,\alpha$-trehalose include the enzymatic methods as disclosed in Japanese Patent Kokai Nos. 143,876/95, 213,283/95, 322,883/95, 298,880/95, 66,187/96, 66,188/96, 336,388/96, and 84,586/96, where non-reducing saccharide-forming enzymes and trehalose-releasing enzymes are allowed to act on starch hydrolysates to form $\alpha,\alpha$-trehalose. The trehalose thus obtained can be advantageously used because of its economical merit and lesser possibility of the contamination of harmful impurities as compared with those prepared by synthetic methods. Examples of commercialized trehalose produced by the above enzymatic methods are "TREHA®", a trehalose having a trehalose content of 98%, on a dry solid basis (d.s.b.), commercialized by Hayashibara Shoji, Inc., Okayama, Japan; and a reagent grade trehalose having a trehalose content of 99% or higher, d.s.b., commercialized by Hayashibara Biochemical Laboratories, Inc., Okayama, Japan. The trehalose usable in the present invention should not be restricted to the ones above, however, the above trehalose products can be advantageously used.

The α,β-trehalose usable in the present invention can be produced, for example, by the method as disclosed in Japanese Patent Kokai No. 179,490/92 where an enzyme is allowed to act on a mixture of starch hydrolysate and lactose, while the β,β-trehalose usable in the present invention can be chemically synthesized easily. The trehalose used in the present invention should not necessarily be in an isolated form or may be in a mixture form of trehalose and other saccharides that are formed during the production of trehalose, as long as they do not spoil the therapeutic and/or prophylactic effect by trehalose on the ophthalmologic clinical symptoms and signs in Sjögren syndrome. Of course, impurities such as pyrogens should preferably be removed by using activated charcoal, ion-exchange chromatography, gel filtration chromatography, and membrane filtration because ophthalmic solutions are directly applied to the ocular-mucous membranes.

When administered to patients with the ophthalmologic clinical symptoms of Sjögren syndrome such as foreign body sensation, burning, and itching, the ophthalmic pharmaceutical composition of the present invention improves the above symptoms and, when administered to patients with inconsistent onset and restoration of the symptoms during a symptomless period, it can prevent the occurring of such symptoms. The ophthalmic pharmaceutical composition of the present invention can be used in the form of an eyewash, ophthalmic solution, or ophthalmic ointment.

The ophthalmic pharmaceutical composition of the present invention can be prepared using commonly used pharmaceutically-acceptable carriers in such a manner of mixing them with an effective amount of trehalose to suit the desired formulation. The carriers used for ophthalmic solutions and eyewashes include any one of those which are commonly used therefor, usually, purified water. The ophthalmic pharmaceutical composition of the present invention can be previously prepared into a solution form or processed into a solid preparation using lyophilization method, etc., to be used after dissolving when in use in such a manner of dissolving the solid preparation in solvents such as purified water and physiological saline. Examples of such a solid preparation include tablets, granules, and powders. To prepare the ophthalmic pharmaceutical composition in the form of an ointment, petrolatum, and propeto for ophthalmic use can be used. These ophthalmic pharmaceutical compositions can be prepared in accordance with conventional methods and should preferably be sterilized before use by conventional methods using membrane filters, autoclaves, etc.

The content of trehalose in the ophthalmic pharmaceutical composition of the present invention is usually set to give a final concentration of at least 0.01% by weight or in the range of about 0.01 to about 30% by weight, preferably, 0.5 to 20% by weight, and most preferably, 2 to 10% by weight from a viewpoint of therapeutic and/or prophylactic effect on both the ocular-mucous membranes and the ophthalmologic clinical symptoms and signs in Sjögren syndrome. The aforesaid concentration of trehalose means the concentration expressed by a percent by weight per volume (w/v) as for liquid eyewashes and ophthalmic solutions, or the concentration expressed by a percent by weight per weight (w/w) as for solid ophthalmic ointments. Since the ophthalmic pharmaceutical composition of the present invention directly contacts with the ocular-mucous membranes, the composition should preferably be set to pHs around neutral pHs, most preferably, pHs of 6.5-7.5 with respect to safety; and should preferably be set to osmotic pressures of about 0.5-4.0, more preferably, 1.0-1.5. The pH and the osmotic pressure of the ophthalmic pharmaceutical composition of the present invention can be controlled by conventional methods.

Among saccharides, trehalose quite stably retains its properties, substantially does not cause the amino carbonyl reaction even when coexisted with-amino-containing vitamins and peptides, or even stabilizes them. Therefore, the ophthalmic pharmaceutical composition of the present invention can be prepared by appropriately combining with one or more ingredients such as saccharides other than trehalose, electrolytes, amino acids, vitamins, lipids, pharmaceutical additives, and pharmaceuticals.

Concrete examples of the ingredients other than trehalose used in the ophthalmic pharmaceutical composition of the present invention are saccharides such as glucose and maltose; sugar alcohols such as mannitol and sorbitol; electrolytes such as sodium chloride, sodium hydrogenphosphate, potassium chloride, magnesium sulfate, and calcium chloride; amino acids such as glycine and alanine; vitamins and derivatives thereof such as thiamine hydrochloride, sodium riboflavin phosphate, pyridoxine hydrochloride, nicotinamide, folic acid, biotin, vitamin A, L-ascorbic acid, and α-glycosyl-L-ascorbic acid, which all can be used in an appropriate combination. Particularly, in the case of the ophthalmic pharmaceutical composition of the present invention is in the form of an ophthalmic solution, the combination use of trehalose as an effective ingredient and one or more other saccharides selected from monosaccharides such as glucose and fructose, disaccharides such as maltose, and oligosaccharides higher than maltotriose tends to more stably exert a satisfactory therapeutic and/or prophylactic effect on the ophthalmologic clinical symptoms and signs in Sjögren syndrome. In this case, the ratio of a saccharide(s) other than trehalose is 0.0001-10 times, preferably, 0.001-5 times, and more preferably, 0.001-2 times of trehalose in an anhydrous form. In addition, one or more of the following additives used in conventional ophthalmic preparations can be used in the ophthalmic pharmaceutical composition of the present invention as long as they do not spoil the present object; preservatives such as methyl p-hydroxybenzoate, sodium dehydroacetate, and benzalkonium chloride; buffers such as borax (sodium borate), boric acid, and sodium hydrogencarbonate; viscosity-imparting agents such as methyl cellulose, carboxy methyl cellulose, chondroitin sulfate, polyvinyl alcohol, and pullulan; solubilizers such as polysorbate 80; and stabilizers such as sodium edetate, and sodium hydrogensulfite. In the ophthalmic pharmaceutical composition of the present invention, the above preservatives such as methyl p-hydroxybenzoate, sodium dehydroacetate, and benzalkonium chloride may not preferably be used because they may induce allergy in some patients.

When the ophthalmic pharmaceutical composition of the present invention is in the form of an ophthalmic ointment, conventional carriers used for ophthalmic ointments can be used; for example, white petrolatum and plastibase for ophthalmic use. The additives used in such an ophthalmic ointment include liquid paraffin. If necessary, the ophthalmic pharmaceutical composition of the present invention can be used in an appropriate combination with steroid hormones such as methylprednisolone; anti-inflammatories such as tetracycline; antiseptics such as penicillin G; immunosuppressants such as cyclosporin; and pharmaceuticals such as immunomodulators, analgesics, autosera, and hyaluronic acid.

The signature-dosage of the ophthalmic pharmaceutical composition of the present invention can be appropriately controlled depending on the symptoms and signs of patients. When used as an ophthalmic solution, the ophthalmic pharmaceutical composition of the present invention is administered to patients at a dose of one to four drops (about 0.025 to about 0.1 ml) per shot one to ten times a day. When used as an eyewash, the ophthalmic pharmaceutical composition of the present invention is usually used in such a manner of pouring an about five milliliters of the eyewash in an exclusive container that can be closely applicable to the face-line around the patient's eyes, applying the container to the face-line, allowing the patients to lean back to face up, and allowing the patients to blink several times to allow to contact their eyes with the composition at a dose of one to six times a day; or used in such a manner of washing their eyes using a washing bottle at a dose of one to five times a day using about one to about five milliliters of the eyewash per shot.

The following examples describe the present invention but do not restrict the present invention:

Example 1

Ophthalmic solution
In 100 ml

| | |
|---|---|
| α, α-Trehalose | 3.5 g |
| Sodium chloride | 0.4 g |
| Potassium chloride | 0.15 g |
| Sodium dihydrogenphosphate | 0.2 g |
| Borax | 0.15 g |
| Sterilized refined water | Balance |
| Total | 100 ml |

The above ingredients are prepared in a usual manner into a sterilized preparation (pH 7.3) as an ophthalmic solution.

Example 2

Ophthalmic solution
In 100 ml

| | |
|---|---|
| α, α-Trehalose | 3.7 g |
| Sodium chloride | 0.4 g |
| D-Glucose | 0.04 g |
| Sterilized refined water | Balance |
| Total | 100 ml |

The above ingredients are prepared in a usual manner into a sterilized preparation (pH 7.2) as an ophthalmic solution.

Example 3

Ophthalmic solution
In 100 ml

| | |
|---|---|
| α, α-Trehalose | 7.0 g |
| D-Glucose | 0.04 g |
| Sterilized refined water | Balance |
| Total | 100 ml |

The above ingredients are prepared in a usual manner into a sterilized preparation (pH 7.3) as an ophthalmic solution.

Example 4

Ophthalmic solution
In 100 ml

| | |
|---|---|
| α, β-Trehalose | 0.5 g |
| Sodium chloride | 0.6 g |
| Potassium chloride | 0.15 g |
| Sodium dihydrogenphosphate | 0.2 g |
| Borax | 0.15 g |
| Benzalkonium chloride | 0.005 g |
| Sterilized refined water | Balance |
| Total | 100 ml |

The above ingredients are prepared in a usual manner into a sterilized preparation (pH 7.0) as an ophthalmic solution.

Example 5

Eyewash
In 100 ml

| | |
|---|---|
| α, α-Trehalose | 0.1 g |
| Sodium chloride | 0.4 g |
| Potassium chloride | 0.05 g |
| Calcium chloride | 0.01 g |
| Magnesium sulfate | 0.01 g |
| Sodium citrate | 0.05 g |
| Sodium bicarbonate | 0.2 g |
| Maltose | 0.15 g |
| 1N-Hydrochloric acid | Balance |
| Sterilized refined water | Balance |
| Total | 100 ml |

The above ingredients are prepared in a usual manner into a sterilized preparation (pH 7.2) as an eyewash.

Example 6

Ophthalmic ointment
In 100 g

| | |
|---|---|
| α, α-Trehalose | 3.5 g |
| Liquid paraffin | 5.0 g |
| White petrolatum for ophthalmic use | Balance |
| Total | 100 g |

The above ingredients are prepared in a usual manner into a sterilized preparation as an ophthalmic ointment.

Experiment

Methods

To confirm the therapeutic effect by trehalose on the ophthalmologic clinical symptoms and signs of Sjögren syndrome, patients consisting of 10 men and 10 women, 22-65 years old (a mean average of 45 years old), who were diagnosed as Sjögren syndrome and had been suffering from clinical symptoms such as foreign body sensation, burning, and itching in their both eyes, were subjected to a therapeutic experiment. In this experiment, a reagent grade of α,α-trehalose with a purity of 99% or higher, commercialized by Hayashibara Biochemical Laboratories, Inc., Okayama, Japan, was dissolved in physiological saline to give a final concentration of 3.5% (w/v) or 7.5% (w/v), and filtered with a 0.22 μm membrane filter to remove bacteria. Then, the filtrate was removed pyrogen in a usual manner for a test preparation. As a control, a similar preparation was provided except for not dissolving α,α-trehalose therein. The 3.5% (w/v) α,α-trehalose solution was administered to one eye for each one of 5-male and 5-female patients, while the physiological saline as a control was administered to the other eye for each one of the patients. The administrations were conducted at four times (getting up, daytime, evening, and before sleeping) a day and at a dose of two to three drops (a volume of about 0.05 to about 0.075 ml) per shot for four weeks. Before and after this experiment, the patients were asked to grade the symptoms of foreign body sensation, burning, and itching in their eyes. Using the 7.5% (w/v) α,α-trehalose solution, a similar experiment was conducted with the remaining male and female patients, five each.

<Results>

A significant therapeutic effect on the subjective symptoms of the patients tested was observed in the patients administered with either of the α,α-trehalose solutions with different concentrations of α,α-trehalose; nine out of ten patients with the α,α-trehalose solutions were improved or even remitted all the ophthalmic symptoms of foreign body sensation, burning, and itching. The therapeutic effect lasted for some days even after the completion of this experiment. As the objective signs, corneal and conjunctival erosions stained by fluorescein and rose bengal were reduced in all the ten patients, and the tear film break-up time was improved in nine out of ten patients. In the control, the ophthalmic symptoms and signs of the patients once tended to remit temporally just after the administration, but recurred before the next administration, and the improvement in their subjective symptoms was not observed. In addition, no improvement in their objective signs was observed in the patients as control and, after completion of the experiment, they still showed substantially the same clinical symptoms and signs as before the experiment. During and after completion of the experiment, all the twenty patients showed no exacerbation of the ophthalmologic clinical symptoms and signs in the eyes administered with the α,α-trehalose solutions, nor did other symptoms and signs diagnosed as side effect or the like.

The ophthalmic pharmaceutical composition of the present invention exerts an outstanding improvement in the ophthalmologic clinical symptoms and signs in Sjögren syndrome, and thus it can be advantageously used in the treatment and/or the prevention of the syndrome. Since trehalose per se is a safe and stable saccharide, the saccharide can be repeatedly administered for a relatively-long period of time without fear of causing side effect.

While there has been described what is at present considered to be the preferred embodiments of the invention, it will be understood the various modifications may be made therein, and it is intended to cover in the appended claims all such modifications as fall within the true spirits and scope of the invention.

What is claimed is:

1. A method for treeing a patient suffering from dry eye, comprising:
   a. introducing a liquid ophthalmic pharmaceutical composition into a container for close application to the face-line around the patient's eye(s), said liquid ophthalmic pharmaceutical composition being in the form of an eyewash free of benzalkonium chloride, having a pH of 6.5 to 7.5 and an osmotic pressure of 0.5 to 4.0, and comprising (i) trehalose as an effective ingredient, (ii) one or more oligosaccharides consisting of more than three glucose molecules in an amount of 0.001 to 2 times of said trehalose, and (iii) an ophthalmologically-acceptable carrier;
   b. applying said container to the face-line of said patient to deliver said liquid ophthalmic pharmaceutical composition to the patient's eye(s); and
   c. allowing the patient to blink several times whereby the patient's eye(s) contacts the liquid ophthalmic pharmaceutical composition,
   whereby the symptoms of dry eye of said patient are improved or remitted.

2. The method according to claim 1 wherein the trehalose is present in the liquid ophthalmic pharmaceutical composition in a final concentration of trehalose of from about 0.01% to about 30% by weight/volume.

3. The method according to claim 2 wherein the trehalose is present in the liquid ophthalmic pharmaceutical composition in a final concentration of trehalose of from 2 to 10% by weight/volume.

* * * * *

UNITED STATES PATENT AND TRADEMARK OFFICE
CERTIFICATE OF CORRECTION

| | |
|---|---|
| PATENT NO. | : 7,732,425 B2 |
| APPLICATION NO. | : 10/393947 |
| DATED | : June 8, 2010 |
| INVENTOR(S) | : Matsuo et al. |

Page 1 of 1

It is certified that error appears in the above-identified patent and that said Letters Patent is hereby corrected as shown below:

At column 8, line 13 (claim 1, line 1), delete the word "treeing" and insert --treating--.

Signed and Sealed this

Fourteenth Day of September, 2010

David J. Kappos
*Director of the United States Patent and Trademark Office*